United States Patent [19]

Bowen et al.

[11] 3,956,044

[45] May 11, 1976

[54] METHOD AND MEANS FOR FABRICATING SURGICAL SPONGES

[75] Inventors: Leonard C. Bowen, Avon; Reginald R. Gallant, Rocky Hill, both of Conn.

[73] Assignee: Surgicot, Inc., New York, N.Y.

[22] Filed: May 15, 1974

[21] Appl. No.: 470,147

[52] U.S. Cl. .............................. 156/73.2; 128/296; 156/191; 156/217; 156/250; 156/270; 156/457; 156/580; 242/60; 242/67.1 R

[51] Int. Cl.² ............................................ B29C 27/08

[58] Field of Search ................ 156/73.1, 73.2, 73.3, 156/73.4, 148, 184, 190, 191, 217, 290, 291, 443, 446, 457, 465, 250, 266, 270, 580; 242/60, 67.1, 86.1, 86; 264/68, 69; 128/156, 296; 53/33, DIG. 2

[56] References Cited

UNITED STATES PATENTS

| 831,726 | 9/1906 | Long | 242/60 |
|---|---|---|---|
| 2,933,262 | 4/1960 | Fish | 242/86.1 |
| 2,972,350 | 2/1961 | Deker | 128/296 |
| 3,558,381 | 1/1971 | Colianni | 156/73.2 |
| 3,575,752 | 4/1971 | Carpenter | 156/73.2 |

OTHER PUBLICATIONS

"New: No Thread, No Needle Ultrasonic Sewing", *Ultrasonic News,* Nov. 1970.

*Primary Examiner*—William A. Powell
*Assistant Examiner*—Jerome W. Massie
*Attorney, Agent, or Firm*—McCormick, Paulding & Huber

[57] ABSTRACT

Surgical sponge material is unwound from a spool and fed onto a horizontal support where it is cut to the proper length, folded once by means of a vertically reciprocable mandrel, and held in an upwardly open cavity between the two tines of a rotatable fork. The fork rolls the sponge in a cylindrical portion of the cavity to form the sponge on the tines of the fork. A pusher strips the sponge from the tines of the fork and moves it into a trough where an ultrasonic welding horn seals the free end of the sponge material to prevent it from unraveling. The sponge material is preferably woven from cotton or the like but includes one or more synthetic threads of thermoplastic material to facilitate the ultrasonic welding step.

9 Claims, 3 Drawing Figures

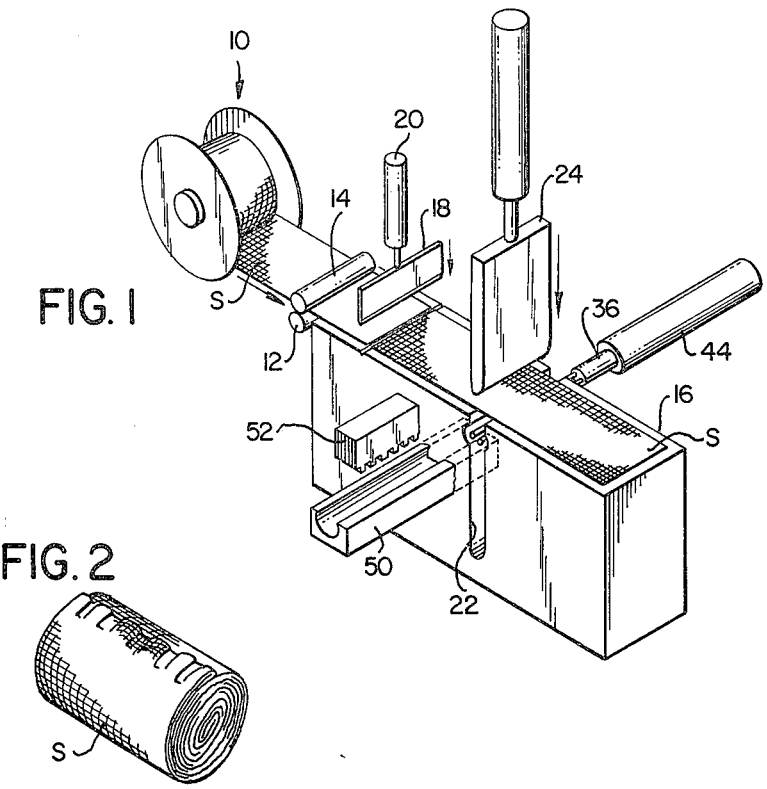
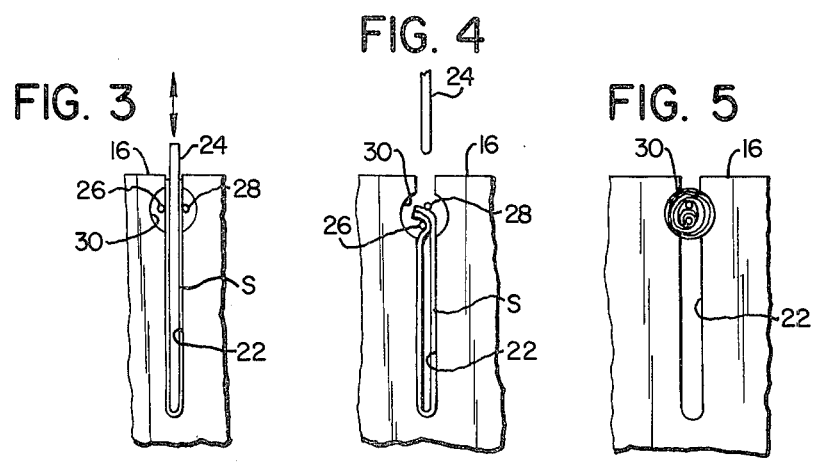
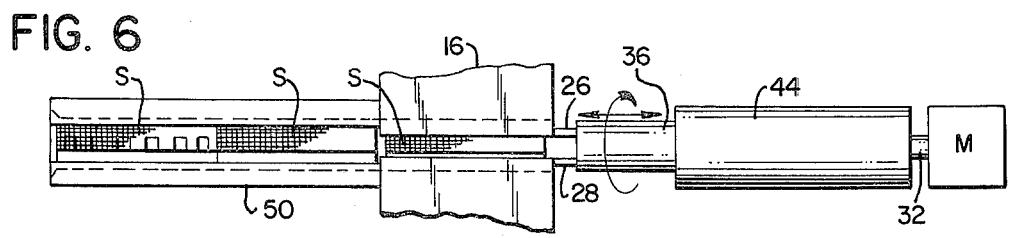

METHOD AND MEANS FOR FABRICATING SURGICAL SPONGES

SUMMARY OF THE INVENTION

This invention relates generally to the fabrication of surgical sponges, and deals more particularly with an automated system for severing the sponge material to form strips of appropriate length, and rolling this material to form the sponges.

The sponge material is conventionally woven into a continuous strip of the desired width, and with one or more threads of synthetic material provided in the strip to permit an ultrasonic final welding step to replace the manual stitching process required heretofore.

Basically, the woven material is provided on a roll, or spool, and driven rollers feed the strip onto a horizontal support, or bed, where a cut-off blade is adapted to sever the strip to provide the desired length of material on the bed. A relatively thin mandrel has a width approximately equal to the strip width, and engages a medial segment of the severed strip to fold it between the side walls of an upwardly open cavity, and also between two tines of a fork located in a enlarged generally cylindrical portion of the cavity. Withdrawal of the mandrel leaves the sponge material folded once in a generally U-shaped configuration between the tines of the fork.

Means is provided for rotating the fork to roll the sponge material around the closely spaced tines, and in the generally cylindrical enlarged portion of the cavity. The sponge in its rolled condition is then stripped from the tines of the fork by a plunger, or pusher, mounted coaxially with the fork and movable into the cylindrical cavity portion so as to displace the rolled sponge and position it in a trough or track below an ultrasonic horn, which horn then welds the synthetic threads to one another and thereby holds the sponge in its rolled configuration.

BRIEF DESCRIPTION OF THE DRAWINGS

FIG. 1 is a perspective view showing in schematic fashion a mechanism for carrying out the method of the present invention.

FIG. 2 is a perspective view of a sponge formed by the method and means of the present invention.

FIGS. 3, 4 and 5 show in sequence the configuration of the woven strip of sponge material as it is folded into a U-shaped configuration and then rolled on the tines of a rotating fork to provide the configuration depicted in FIG. 2.

FIG. 6 is a plan view of a portion of the apparatus depicted in FIG. 1 and shows a sponge rolled in the configuration shown in FIG. 5.

DETAILED DESCRIPTION

Figure 7:
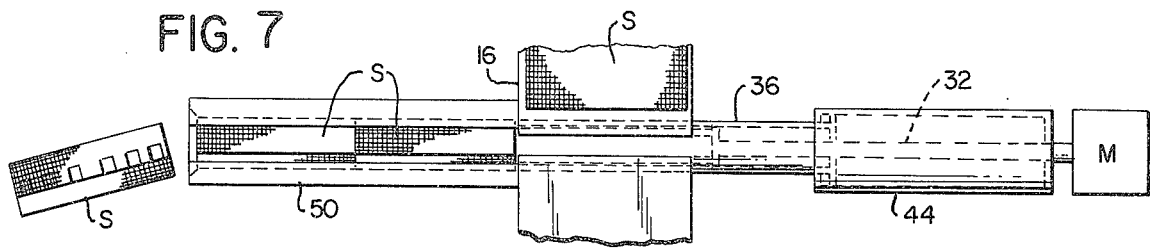
FIG. 7 is a plan view of the portion of the apparatus shown in FIG. 6 at a slightly later instant of time.

Surgical sponges are generally woven specifically for the intended purpose, namely for operating room use in hospitals or the like, and the sponge material is conventionally woven from cotton or other absorbent material to a specific width generally on the order of one inch. The material is so woven in order to provide a width defined by marginal edges which are not characterized by loose ends or the like. This material is available commercially on rolls or spools with a treated thread woven into the material such that a particular sponge can be traced when one is left, inadvertently, in a patient after an operation. For example, providing a particular thread material will permit the sponge to be located by means of an x-ray machine or the like. Conventional sponge fabricating techniques call for cutting sponge material to a desired length, rolling the material to form a sponge, and then manually stitching the sponge to hold it in its cylindrical configuration.

The present invention discloses an improved mechanism for fabricating these surgical sponges from the continuous strip form in which this material is currently available. However, it is also noted that in order to realize the full advantage of the present invention this sponge material is preferably provided with one or more threads of synthetic material, which threads can be welded by present day ultrasonic techniques, such as the SONIFIER available from Branson Sonic Power Company, Eagle Road, Danbury, Connecticut.

Turning now to the drawings in greater detail, and referring particularly to FIG. 1, a roll or spool of sponge material is indicated generally at 10, and such material is preferably woven with smooth marginal edges and with a suitable tracer thread in accordance with present practices. In accordance with the present invention, the material also includes one or more synthetic threads of thermoplastic material well suited for the ultrasonic welding process to be described in greater detail hereinbelow. In further accordance with the present invention, the strip of sponge material is intermittently fed from the roll 10 by selectively driven rolls 12 and 14 onto the upper surface of a support table or bed 16. The rolls 12 and 14 are intermittently driven, and the sponge material may be fed against a stop, or for a predetermined time in order to provide a known length of material on the upper surface of the bed 16.

A vertically reciprocable cutter 18 is provided above the path of travel of the strip of sponge material S so as to sever the material in timed relationship with operation of the feeder rolls 12 and 14. As indicated schematically at 20 in FIG. 1 motor means is provided for reciprocating the cutter blade 18.

As best shown in FIGS. 3, 4 and 5 an upwardly open cavity 22 is defined in the support bed 16. A vertically reciprocable mandrel 24 is movable from and to the limit positions shown in FIGS. 3 and 4 whereby to fold the strip of sponge material S into a generally U-shaped configuration in the cavity 22 and between the tines 26 and 28 of a fork structure to be described.

Still with reference to the generally upwardly open cavity 22, an enlarged generally cylindrical upper portion of the cavity is indicated generally by the reference numeral 30, and it will be noted from FIGS. 3, 4 and 5 that the tines 26 and 28 of the fork structure are located in generally centered relationship with respect to said upper cylindrical cavity portion 30. The longitudinal axis of such cavity portion 30 is oriented at right angles to the longitudinal dimension of the upwardly open cavity 22. The tines 26 and 28 are arranged in side-by-side horizontally spaced relationship in the cavity portion 30 and the vertically reciprocable mandrel 24 is adapted to urge the strip S of sponge material downwardly between the tines in this preliminary stage of fabrication of the sponge. When the mandrel 24 is withdrawn from the cavity 22, as shown in FIG. 4, the tines 26 and 28 are adapted to rotate, and to thereby twist or roll the strip of sponge material around the tines as best shown in FIG. 5.

Figure 8:
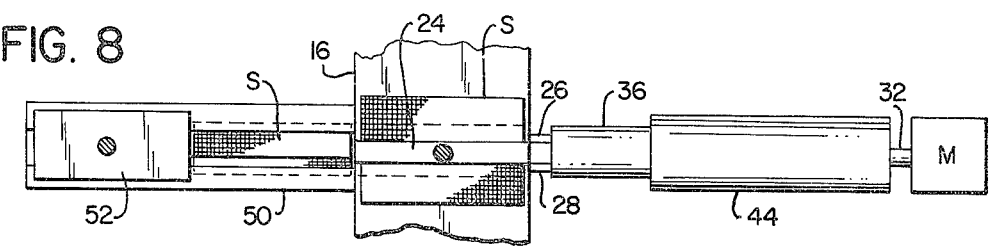
FIG. 8 shows the apparatus of FIG. 7 at a slightly later instant of time and during a preliminary stage of forming a succeeding sponge.

While the fork structure is shown to some extent in FIG. 1, FIGS. 7, 8 and 9 illustrate to better advantage the mode of operation of this fork structure. As shown in FIG. 8 for example, the vertically reciprocable mandrel 24 is adapted to move downwardly between the tines 26 and 28 during the initial forming stage referred to above. The tines 26 and 28 are adapted to be rotated for a predetermined number of revolutions, depending upon the longitudinal extent of the strip S of sponge material, and a motor M has an extended drive shaft 32 drivingly connected to the base of the fork structure as indicated generally at 34 in FIG. 9.

Figure 9:
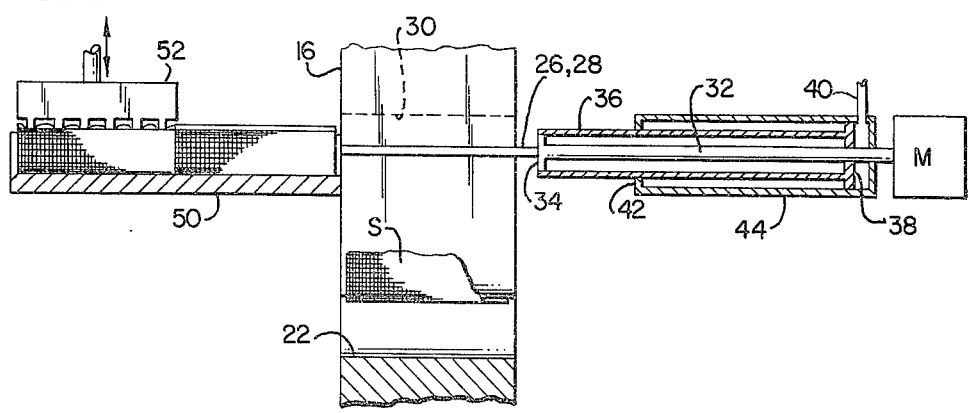
FIG. 9 is an elevational view partly in section of the mechanism shown in FIG. 8.

Once the sponge material has been wound on the tines of the fork, as best shown in FIG. 5, means is provided for stripping the sponge from the fork tines and for moving the rolled sponge from its cavity 30 to a succeeding station where the free end of sponge material can be suitable secured to avoid unrolling of the sponge. Preferably, and as best shown in FIGS. 7, 8 and 9 a plunger or pusher 36 is provided in co-axial relationship to the axis of rotation of the fork structure and the said pusher is adapted to move from the position shown in FIGS. 8 and 9 to that of FIG. 7 whereby to move the rolled sponge out of its associated cavity. While any suitable means might be adapted for use in reciprocating the pusher 36, FIG. 9 shows the pusher 36 as comprising a generally tubular element having an inner head portion 38 against which fluid under pressure acts in line 40 to selectively urge the pusher from the position shown for it in FIG. 9 to that of FIG. 7. The pusher 36 is spring returned by suitable means (not shown) and is also supported at its outer end by means of the head portion 42 of the outer cylinder structure 44 in which the head portion 38 is slidably received as shown in FIG. 9. This cylinder portion 44 need not rotate with the motor shaft 32 and the tubular pusher element 36 may or may not rotate with this shaft during rolling of the sponge material but in the embodiment shown it is noted that this pusher 36 does not so rotate.

As suggested in FIG. 7 the line pressure created by the forming of succeeding sponges can be used to eject a finished sponge from a trough 50 best shown in FIG. 1, which trough is adapted to receive the rolled sponges in a position wherein each can be acted upon by an ultrasonically vibrating horn 552, which horn is also vertically reciprocable for movement from and to an active position as suggested in FIG. 9. The horn 52, when in its active position, welds the synthetic threads in the sponge material to prevent unrolling of the sponge as mentioned above. The horn 52 may be made of sufficient extent so as to weld one or more such sponges simultaneously, or the horn 52 may be made of sufficient length so as to weld only one such sponge as shown in FIG. 9. While the trough 50 is shown as being upwardly open, the portion of the trough between the horn 52 and the bed 16 may be enclosed to provide a cylindrical passageway for holding the rolled sponges in a rolled configuration until each has been suitably welded. It will be apparent that such a circular passageway for the rolled sponges might be made of any desired length so as to set the rolled sponge into its coiled configuration prior to the actual sonic welding stop.

The welding horn associated with the ultrasonic process may be formed with grooves as shown in FIG. 9 and as a result impart to the rolled and welded sponge of FIG. 2 a characteristic pattern at the point where the welding actually occurs.

We claim:

1. A method for fabricating surgical sponges and comprising in combination the steps of:
   a. providing a continuous strip of woven sponge material on a spool or the like,
   b. unreeling said strip from said spool to provide a length of said strip on a horizontal support,
   c. cutting said strip to a predetermined length,
   d. moving a medial segment of said strip into an elongated vertically extending cavity so that portions of the strip are generally vertically disposed in the cavity, and so that the ends of the strip are adjacent one another, and
   e. rolling the strip starting at the adjacent ends so that the medial segment is on the outside of the roll.

2. The method of claim 1 wherein said strip of woven sponge material includes at least one longitudinally extending thread of synthetic thermoplastic material, and wherein said roll is welded in the area of said medial segment by a ultrasonic horn.

3. The method of claim 2 wherein said step of rolling the strip more specifically comprises rotating a pair of fork tines located in an enlarged cylindrical portion of said elongated cavity, and stripping said roll from the tines prior to said welding step.

4. An apparatus for fabricating surgical sponges and comprising:
   a. support means for receiving a length of woven sponge strip,
   b. vertically reciprocable means for engaging a medial segment of said strip intermediate its ends,
   c. elongated cavity defining structure in the path of movement of said vertically reciprocable means for receiving the strip and folding it in the cavity in response to movement of said reciprocable means in one direction,
   d. said cavity defining structure further including a generally cylindrical enlargement thereof, the axis of which enlargement is perpendicular to the longitudinal dimension of said elongated cavity, and
   e. fork means selectively rotatable on said axis, said fork means including two tines between which said vertically reciprocable means is adapted to fold said strip in said cavity when said fork means is not rotating.

5. Apparatus according to claim 4 further characterized by means for stripping the rolled strip from said tines and out of said cavity enlargement.

6. Apparatus according to claim 4 further characterized by trough means for receiving the rolled strip as it is stripped from said tines.

7. Apparatus according to claim 6 further characterized by means for bonding the free edge of said rolled strip to prevent it from unraveling while it is in said trough.

8. Apparatus according to claim 4 wherein said strip of woven material includes at least one thread of synthetic thermoplastic material, and means for ultrasonically welding the free edge of said rolled strip.

9. Apparatus according to claim 7 wherein said strip of woven material includes at least one thread of synthetic thermoplastic material, and said bonding means comprising an ultrasonic welding horn vertically movable above said trough and engageable with the free edge of said rolled strip to weld said thread.

* * * * *